United States Patent [19]

Kitano et al.

[11] 3,974,291

[45] Aug. 10, 1976

[54] FUNGICIDAL COMPOSITIONS FOR DERMATOMYCOSIS OF ANIMALS

[75] Inventors: Noritoshi Kitano, Tokyo; Fusao Kondo, Urawa; Kenichi Kusano; Keijiro Ishibashi, both of Tokyo, all of Japan

[73] Assignee: Sankyo Company Limited, Tokyo, Japan

[22] Filed: Dec. 11, 1974

[21] Appl. No.: 531,717

[30] Foreign Application Priority Data
Jan. 26, 1974  Japan............................. 49-11147

[52] U.S. Cl. ................................................ 424/283
[51] Int. Cl.² ........................................... A61K 31/35

[58] Field of Search ..................................... 424/283

[56] References Cited
OTHER PUBLICATIONS

Chemical Abstracts 57: 16753e (1962).
Chemical Abstracts 58: 6158e (1963).
The Merck Manual, 12 Ed., 1972, pp. 1450–1453.

*Primary Examiner*—Stanley J. Friedman
*Attorney, Agent, or Firm*—Flynn & Frishauf

[57] ABSTRACT

Fungicidal compositions for topical treatment of dermatomycosis of animals which contain as active ingredient an antibiotic substance siccanin, preferably in the form of an aerosol or an ointment.

3 Claims, No Drawings

FUNGICIDAL COMPOSITIONS FOR DERMATOMYCOSIS OF ANIMALS

This invention relates to a new use of an antibiotic substance as a veterinary medicine against dermatomycosis of animals.

More particularly, it relates to a new fungicidal composition for the topical treatment of dermatomycosis of animals and also to a new method for the treatment of dermatomycosis of animals.

Still more particularly, it is concerned with a fungicidal composition which comprises, as an active ingredient, an antibiotic substance siccanin having the structural formula

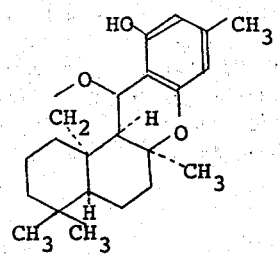

and a suitable carrier and also with a method for the treatment of dermatomycosis of animals which comprises applying siccanin to animals suffering from dermatomycosis at their attacked lesions.

Dermatomycosis of animals is generally called ringworm and is a skin disease caused by various dermatophytes. The disease occurs on skins of various animals such as horse, cow, pig, dog, cat, monkey, goat and chicken and appendages of skins such as hair, feather or claw. In the disease, there is recognized clinical finding of circular alopecia and thickened crust. Treatment of the disease is important not only for health of animals but also in the matters of public health, as the disease is infective to both human beings and animals.

Hitherto, physiotherapy, topical treatment and internal administration treatment have been applied to the treatment of dermatomycosis, but satisfactory curing effects have not been obtained by topical treatment agents.

As a result of our extensive studies in order to find out a new and more effective agent for the treatment of dermatomycosis of animals, we have found that an antibiotic substance siccanin is highly effective against dermatomycosis of animals and this invention has been completed upon the above finding.

It is, accordingly, a primary object of this invention to provide a new and effective fungicidal composition which comprises, as an active ingredient, an antibiotic substance siccanin and a suitable carrier.

Other objects and advantages of this invention will become apparent from the following disclosure.

The antibiotic substance siccanin is a known antibiotic substance which is produced by a microorganism *Helminthosporium siccans* and shows a growth inhibiting action against fungi and bacteria, as disclosed in Japanese Pat. No. 3548/1962. In particular, it was known that siccanin has an antifungal activity against pathogenic fungi in human beings and, particularly, an effectiveness against water-eczema (*Tinea pedis*). However, it should be noted that there was not previously reported an effectiveness against dermatophytes which cause dermatomycosis in animals.

The particulars about the chemical structure and physico-chemical properties of siccanin are described in Tetrahedron Letters, No. 23, 2177(1967).

As explained hereinabove, we have first found that siccanin has a strong antifungal activity against pathogenic fungi causing dermatomycosis of animals and proved its effectiveness as a treating agent against dermatomycosis of animals by various practical field tests.

For the purpose of demonstrating a high effectiveness of siccanin against various dermatophytes, minimum inhibitory concentrations of siccanin are summarized hereinbelow with the indicated pathogenic fungi.

Minimum Inhibitory Concentrations ($\mu g/ml$)

| | Pathogenic fungi | 2 days | 4 days |
|---|---|---|---|
| 1. | *Trichophyton equinum* (in horses) | 0.2 – 0.8 | 0.8 |
| 2. | *Trichophyton verrucosum* (in cows) | 0.2 – 0.8 | 0.8 |
| 3. | *Microsporum nanum* (in pigs) | 0.8 | 1.6 |
| 4. | *Trichophyton gallinae* (in chickens) | 0.2 – 0.8 | 0.8 |
| 5. | *Microsporum canis* (in dogs) | 0.8 | 1.6 |

[Note]
(1) MIC measured after 2 days and 4 days on Sabouraud's glucose agar medium in a continuous agar dilution method.
(2) 0.2 – 1.000 $\mu g/ml$ of siccanin in medium.
(3) Cultivation effected at 25°C and siccanin dissolved in dimethylformamide (final concentration of 10%) and diluted.

For practical applications, the antibiotic substance siccanin may be favourably utilized in various preparations for topical application such as in the form of an aerosol, an embrocation agent, an ointment, a medicated bath agent and the like and the aerosol and ointment are most preferable. These preparations may be easily formulated and prepared by those skilled in the art in a conventional method, using a commonly employed carrier.

The preparations or compositions of this invention may also include one or more of the following additives commonly employed in the art, such as a solvent, e.g., ethanol or glycol salicylate; a keratolytic agent, e.g., salicylic acid; a known other fungicide, e.g., pentachlorophenol; and a known other antibiotic substance, e.g., griseofulvin.

The amount of the active ingredient to be added to the present preparation is usually within a range of 0.01–5% (w/v) and preferably of 0.1–0.2% (w/v).

The preparation is usually applied to the infected animals at their lesion parts for about 2–14 days.

In practising the present method, one may easily apply the composition of this invention to the infected animals, for example, by spraying the present composition onto lesion parts in the case of an aerosol or by manual application of the present composition to lesion parts in the case of an ointment. The composition is usually applied once a day, but many more times applications per day may be made upon the type and severity of a disease, the kind of animal to be treated and other factors.

The examples of this invention and the field tests of the present compositions will be more fully illustrated as hereinbelow.

EXAMPLE 1

Aerosol

An aerosol was prepared according to the following formula.

| Ingredient | Weight (g) |
|---|---|
| Siccanin | 1 |
| Ethylene glycol salicylate | 16 |
| Ethanol | 28 |
| Freon 11 (trade name, monofluoro-trichloromethane) | 35 |
| Freon 12 (trade name, difluoro-dichloromethane) | 35 |
| Total | 115 g |

The aerosol prepared as above was sprayed onto dairy cattle and horses at their lesions of dermatomycosis. The spray treatment was effected once a day for continuous 7 days or once a day five times every day. Curative effects after 3 weeks and 4 weeks from the initiation of the treatment are summarized as follows:

I. Curative effect on dairy cattle
 1. Continuous sprayings once a day for 7 days.

| Test place | No. of animals | Effectiveness 3 weeks | 4 weeks |
|---|---|---|---|
| Farm A | 8 | 6 animals cured | all cured |
| Farm B | 5 | 4 " | " |
| Farm C | 9 | 8 " | " |

2. Five times sprayings once a day every day.

| Test place | No. of animals | Effectiveness 3 weeks | 4 weeks |
|---|---|---|---|
| Farm B | 5 | 4 animals cured | all cured |
| Farm C | 9 | 7 " | " |

II. Curative effect on horses.
 1. Continuous sprayings once a day for 7 days.

| Test place | No. of animals | Effectiveness 3 weeks | 4 weeks |
|---|---|---|---|
| Farm A | 13 | 10 animals cured | all cured |
| Farm B | 8 | 6 " | " |

2. Five times sprayings once a day every day.

| Test place | No. of animals | Effectiveness 3 weeks | 4 weeks |
|---|---|---|---|
| Farm A | 12 | 7 animals cured | 10 animals cured, 2 animals recurred |
| Farm B | 8 | 5 animals cured | 7 animals cured, 1 animal recurred |

EXAMPLE 2

Ointment

An ointment was prepared according to the following formula.

| Ingredient | Weight (g) |
|---|---|
| Siccanin | 1 |
| Ethylene glycol salicylate | 45 |
| Diisopropyl adipate | 45 |
| Silicic anhydride | 7 |
| Tween 60 | 2 |
| Total | 100 |

The ointment prepared as above was applied to dairy cattle and horses at their lesions of dermatomycosis. This treatment was effected continuously once a day for continuous 7 days or once a day five times every day. After 3 and 4 weeks from the initiation of the treatment, curative effects are summarized as follows:

I. Curative effect on dairy cattle
 1. Continuous applications once a day for 7 days.

| Test Place | No. of animals | Effectiveness 3 weeks | 4 weeks |
|---|---|---|---|
| Farm A | 7 | 6 animals cured | all cured |
| Farm B | 4 | 3 " | " |
| Farm C | 11 | 9 " | 10 animals cured, 1 animal recurred |

2. Five times applications once a day every day.

| Test Place | No. of animals | Effectiveness 3 weeks | 4 weeks |
|---|---|---|---|
| Farm A | 7 | 4 animals cured | 5 animals cured, 2 animals recurred |
| Farm C | 9 | 5 animals cured | 3 animals cured, 6 animals recurred |

II. Curative effect on horses
 1. Continuous applications once a day for 7 days.

| Test Place | No. of animals | Effectiveness 3 weeks | 4 weeks |
|---|---|---|---|
| Farm A | 11 | 7 animals cured | 9 animals cured, 2 animals recurred |
| Farm B | 9 | 5 animals cured | 8 animals cured, 1 animal recurred |

2. Five times applications once a day every day.

| Test place | No. of animals | Effectiveness 3 weeks | 4 weeks |
|---|---|---|---|
| Farm A | 8 | 5 animals cured | 7 animals cured, 1 animal recurred |
| Farm B | 8 | 4 animals cured | 6 animals |

-continued

| Test place | No. of animals | Effectiveness | |
|---|---|---|---|
| | | 3 weeks | 4 weeks |
| | | | cured, 2 animals recurred |

It will be apparent from the above results that the compositions of this invention are highly effective against dermatomycosis of animals.

What is claimed is:

1. A method for the treatment of animal dermatomycosis caused by *Trichophyton verrucosum*, which comprises administering topically to an animal so infected a composition comprising an amount sufficient to inhibit said dermatomycosis of siccanin together with a dermatologically acceptable carrier therefor.

2. The method of claim 1, wherein the carrier is selected from the group consisting of ethanol, glycol salicylate and mixtures thereof.

3. The method of claim 1, wherein the amount of siccanin is from 0.01 to 5 percent (w/v) thereof.

* * * * *